United States Patent
Neumann et al.

(10) Patent No.: US 11,360,062 B2
(45) Date of Patent: Jun. 14, 2022

(54) METHOD FOR RAPID DIFFERENTIAL DIAGNOSIS OF INFECTION USING SUPERCRITICAL FLUID CHROMATOGRAPHIC SEPARATION OF MICROBIAL QUORUM SENSING MOLECULES

(71) Applicants: Aaron Neumann, Albuquerque, NM (US); Linnea K. Ista, Albuquerque, NM (US)

(72) Inventors: Aaron Neumann, Albuquerque, NM (US); Linnea K. Ista, Albuquerque, NM (US)

(73) Assignee: UNM Rainforest innovations, Albuquerque, NM (US)

( * ) Notice: Subject to any disclaimer, the term of this patent is extended or adjusted under 35 U.S.C. 154(b) by 901 days.

(21) Appl. No.: 15/883,386

(22) Filed: Jan. 30, 2018

(65) Prior Publication Data
US 2018/0231512 A1 Aug. 16, 2018

Related U.S. Application Data

(60) Provisional application No. 62/451,849, filed on Jan. 30, 2017.

(51) Int. Cl.
*G01N 30/86* (2006.01)
*C12Q 1/04* (2006.01)
*G01N 30/88* (2006.01)
*G01N 30/72* (2006.01)

(52) U.S. Cl.
CPC .......... *G01N 30/8631* (2013.01); *C12Q 1/04* (2013.01); *G01N 30/7233* (2013.01); *G01N 30/8675* (2013.01); *G01N 2030/8813* (2013.01); *G01N 2333/21* (2013.01); *G01N 2333/40* (2013.01); *G01N 2430/00* (2013.01); *G01N 2800/26* (2013.01)

(58) Field of Classification Search
CPC .. C12Q 1/04; G01N 30/7233; G01N 30/8631; G01N 30/8675; G01N 2333/21; G01N 2333/10; G01N 2800/26
See application file for complete search history.

(56) References Cited

PUBLICATIONS

Struss et al. (Anal. Chem., 2013, 85:3355-3362) (Year: 2013).*
Rutherford and Bassler (Cold Spring Harb. Perspect. Med., 2012, 2:a012427) (Year: 2012).*
Gregus et al. (Journal of Pharmaceutical and Biomedical Analysis, 2010, 53:674-681) (Year: 2010).*
Perrenoud et al. (Journal of Chromatography A, 2012, 1266:158-167) (Year: 2012).*
Rios et al. (Bioanalysis, 2010, 2(1):9-25) (Year: 2010).*
Weber et al. (American Society for Microbiology, 2008, p. 1859-1861) (Year: 2008).*
Nickerson et al. (Applied and Environmental Microbiology, 2006, p. 3805-3813) (Year: 2006).*
Bose et al. (FEMS Microbiology Letters, published Jan. 13, 2017, 364:fnx002) (Year: 2017).*

(Continued)

*Primary Examiner* — Jeremy C Flinders
(74) *Attorney, Agent, or Firm* — Gonzales Patent Services; Ellen M. Gonzales

(57) ABSTRACT

A method for rapid differential diagnosis of infection using supercritical fluid chromatographic separation of quorum sensing molecules as biomarkers for infection agents.

8 Claims, 15 Drawing Sheets

Retention Time (min)

(56) References Cited

PUBLICATIONS

Ortori et al. (Pseudomonas Methods and Protocols, Methods in Molecular Biology, vol. 1149, Chapter 21, DOI 10.1007/978-1-4939-0473-0_21) (Year: 2014).*

Williams et al. (Phil. Trans. R. Soc. B, 2007, 362:1119-1134) (Year: 2007).*

Duncan et al. (Lipids, 2008, 43:619-627) (Year: 2008).*

Purohit et al., "Presence of acyl-homoserine lactones in 57 members of the Vibrionaceae family" Journal of Applied Microbiology 115, 835-847 2013.

* cited by examiner

METHOD FOR RAPID DIFFERENTIAL DIAGNOSIS OF INFECTION USING SUPERCRITICAL FLUID CHROMATOGRAPHIC SEPARATION OF MICROBIAL QUORUM SENSING MOLECULES

CROSS-REFERENCE TO RELATED APPLICATIONS

The following application claims benefit of U.S. Provisional Application No. 62/451,849, filed Jan. 30, 2017, which is hereby incorporated by reference in its entirety.

BACKGROUND

Microbial infections (i.e. those caused by fungi, bacteria and/or viruses) can present life-threatening circumstances, especially in already comprised populations. Rapid identification of the infectious organism (or even the type of infectious organism) can direct the application of the most effective therapy at an earlier stage, when it will be most effective and even lifesaving. Most current microbiological diagnostic tests require prior culture of the infectious organism, which is a process that often takes 24-48 h or more. Some patient populations are especially vulnerable to infection and stand in great need of rapid diagnostics. For instance, cancer patients receiving cytotoxic antineoplastic therapies are at high risk for infection due to neutropenic status, which compromises innate immune inflammatory responses, and frequent occurrence of mucositis, which allows translocation of pathogens across mucosal surfaces. 70% of these patients require emergent care and ~23% of those present with fever/febrile neutropenia. Empiric antimicrobial therapy should be initiated within an hour of triage, and each hour of delay is associated with an 18% increase in mortality. *P. aeruginosa*, *S. aureus* and *C. albicans* are all common causes of febrile neutropenia, each requiring different antibiotics for appropriate coverage. Meningitis also requires rapid initiation of empiric therapy to avoid high risk of mortality.

Accordingly, there is a need for a rapid differential diagnosis of infection that does not require time-consuming culture of the infectious organism.

SUMMARY

According to an embodiment the present disclosure provides a method for rapid differential diagnosis of infection using supercritical fluid chromatographic separation of biomarkers that can be used to identify infection agents. According to a further embodiment, those biomarkers may be or include quorum sensing molecules.

DETAILED DESCRIPTION

Figure 1:
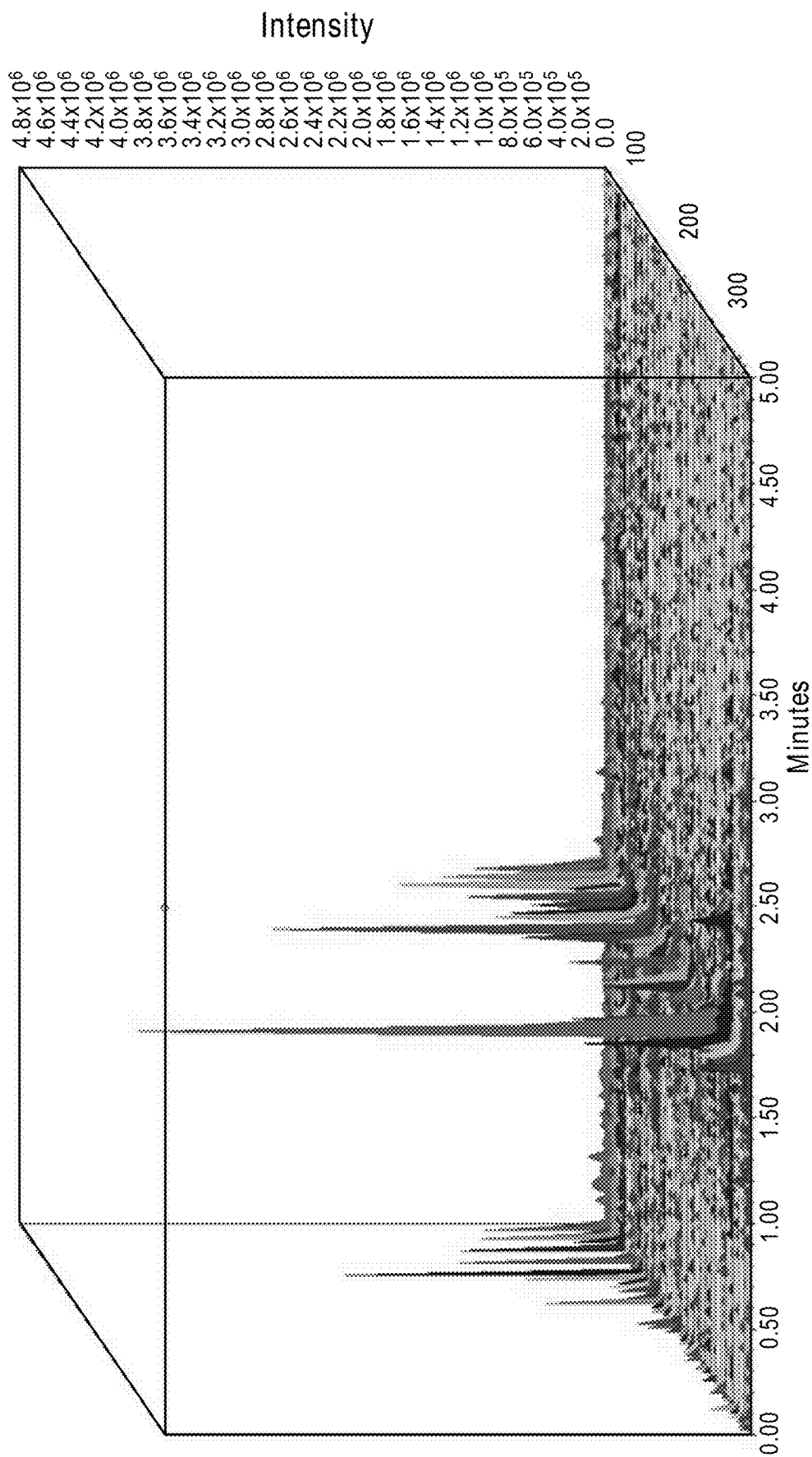
FIG. 1 is a three-dimensional chromatogram resulting from SFC/MS analysis of the QSM farnesol.

According to an embodiment the present disclosure provides a method for rapid differential diagnosis of infection using supercritical fluid chromatographic separation of biomarkers that can be used to identify infection agents.

According to a specific embodiment, the present disclosure provides a method for rapid differential diagnosis of infection using supercritical fluid chromatographic separation of quorum sensing molecules (QSMs). However, it will be understood that other small secondary metabolites including, but not limited to, antibiotics, pigments and redox compounds could also serve as potential targets for diagnosis and/or analysis using the techniques described herein.

Pathogenic Gram-negative bacteria, Gram-positive bacteria and fungi secrete small QSMs that regulate microbial populations via communication both within and between species boundaries. *Pseudomonas aeruginosa*, *Staphylococcus aureus* and *Candida albicans* are common infectious agents that span the spectrum of Gram-negative bacteria, Gram-positive bacteria and fungi. Their QSMs are well-characterized and chemically distinct, making them potentially good biomarkers. *P. aeruginosa* produces a variety of acyl homoserine lactones (AHL) and quinolone compounds that regulate biofilm formation, bacterial motility and invasiveness as well as phenazine toxins (i.e., pyocyanin). *S. aureus* relies on autoinducing peptides (AIP), which are short peptides with a thiolactone ring modification that promote acquisition of virulence traits. *C. albicans* secretes the small organic alcohol QSMs farnesol and tyrosol, which regulate the yeast to hyphal morphological transition that is key to tissue invasion.

The present disclosure describes a technique for QSM detection in specimens, such as clinical specimens (i.e., blood, cerebrospinal fluid, sputum, etc.) as biomarkers of infection. According to an embodiment, the presently disclosed method uses supercritical fluid chromatography (SFC)/mass spectrometry (MS) as the analytical method to detect QSMs in these samples due to its high chromatographic resolution, speed of separation, and specificity of identification of QSM fragments by MS. SFC/MS separation and identification of the microbial metabolites farnesol, pyocyanin, 3-oxo-C12-homoserine lactone and C4-homoserine lactone in individual solutions and mixtures of solutions of the above compounds on a reverse phase column is shown herein. Moreover, separation of peaks may be tuned as desired by using co-solvents, such as Methanol or Acetonitrile with 0.1% formic acid. Furthermore, mass spectrometer operating parameters such as capillary voltage, cone voltage and cone gas flow rate can be tuned to optimize detection of diagnostic ions of the above compounds.

According to a specific embodiment, a specimen for testing/analysis is obtained. In general, the specimen may be obtained directly from a patient (e.g., a blood, cerebrospinal fluid sputum or other sample) or from, for example, a medical device or other apparatus that has been or will be in contact with a patient. Alternatively, a specimen may be obtained from non-clinical settings including, but not limited to home environments and apparatuses such as HVAC systems, evaporative coolers, drywall, plumbing, wells, swimming pools and associated apparatus, water softeners, or other places/apparatuses where it may be desirable to detect and/or identify microbes.

QSMs, if present, are then extracted from the sample. According to an embodiment, QSMs may be extracted by removing protein/lipid contaminants via precipitation and extraction techniques. According to a specific non-limiting example, the sample is initially precipitated and extracted using, for example, an equal volume of acetonitrile. The resulting extract is treated with acidified acetonitrile to precipitate remaining proteins and extracted with, for example, an equivalent volume of ethyl acetate acidified by supplementing with 0.01% acetic acid. The mixtures are then shaken, and the organic phases removed. The pool of ethyl acetate containing the QSMs is then evaporated to dryness and reconstituted in a solvent, such as methanol, for SFC/MS analysis. Of course, other mechanisms for extracting and/or isolating the QSMs prior to SFC/MS analysis may be employed including, but not necessarily limited to chemical extraction with other solvents or affinity based purification.

The solvent in which the QSMs are reconstituted or otherwise dissolved should be appropriate for SFC/MS analysis and may be selected to optimize separation and detection of the specific QSMs being detected. For example, organic cosolvents can be added in varying types, amounts, and gradient profiles to tune chromatographic separation. Non-limiting examples of cosolvents that may useful include methanol and acetonitrile or methanol with 0.1% formic acid.

Figure 2:
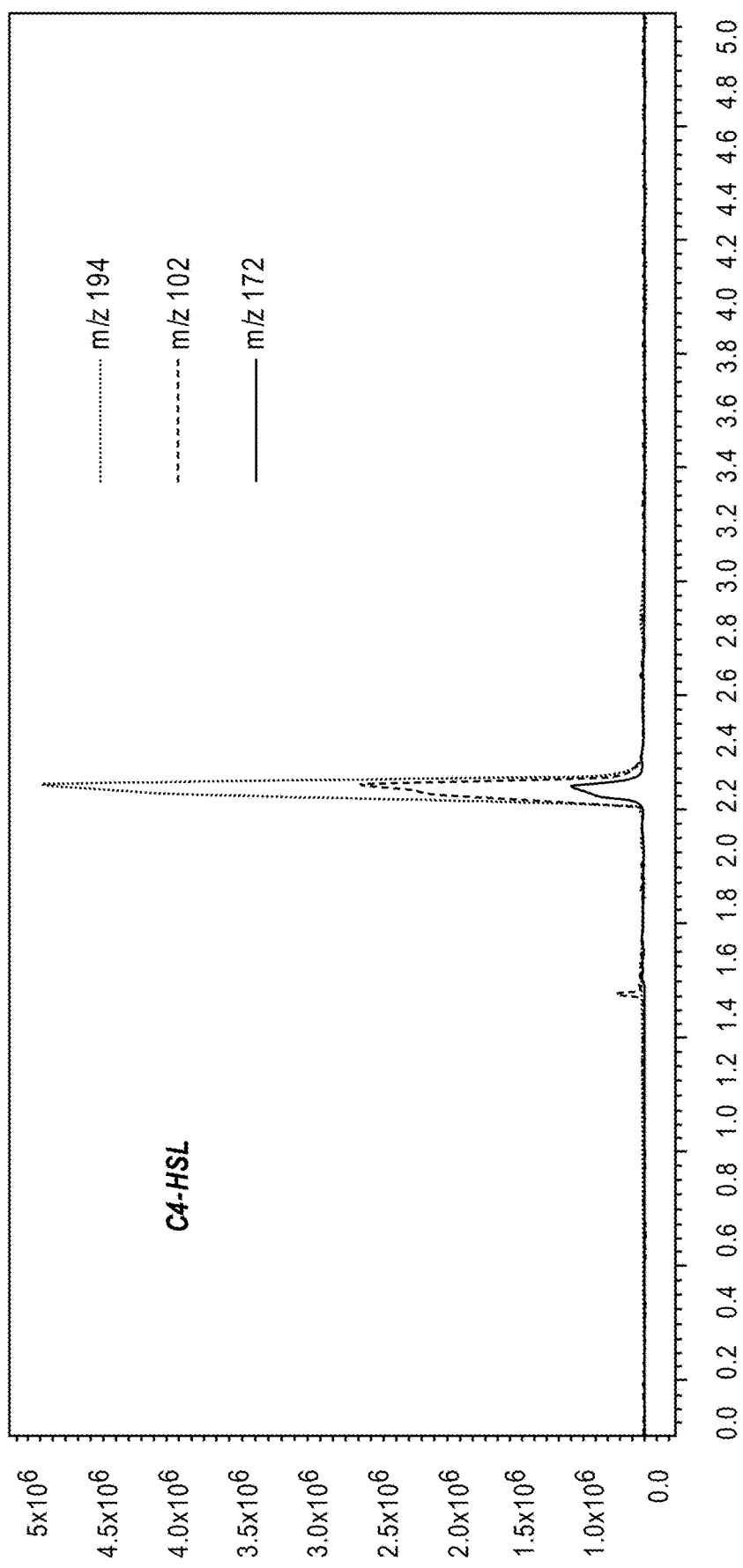
FIG. 2 is a chromatograph resulting from SFC/MS analysis of the QSM N-Butyryl-DL-HSL (C4-HSL).
Figure 3:
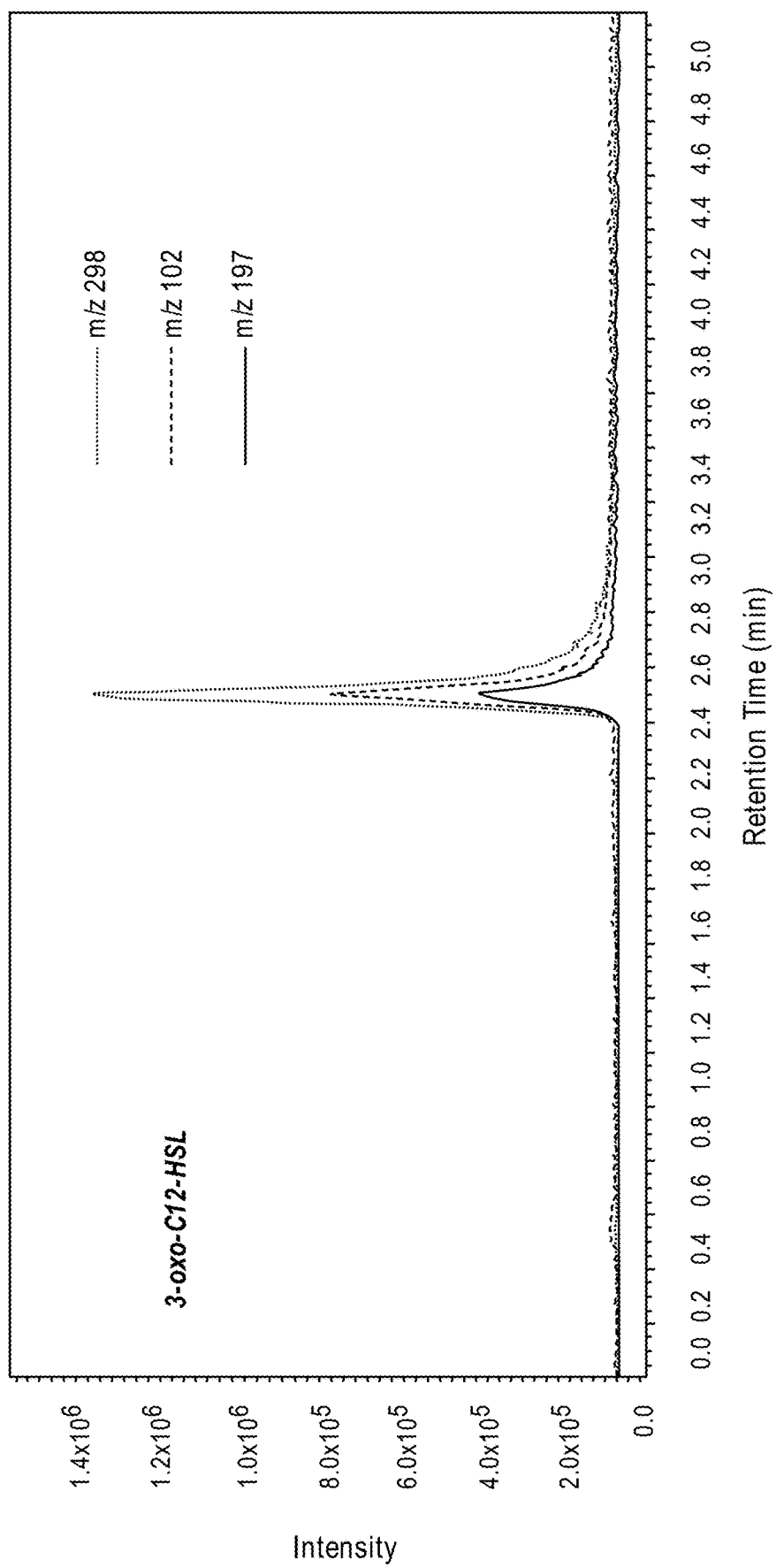
FIG. 3 is a chromatograph resulting from SFC/MS analysis of the QSM 3-Oxo-C12-HSL (C12-HSL).
Figure 4:
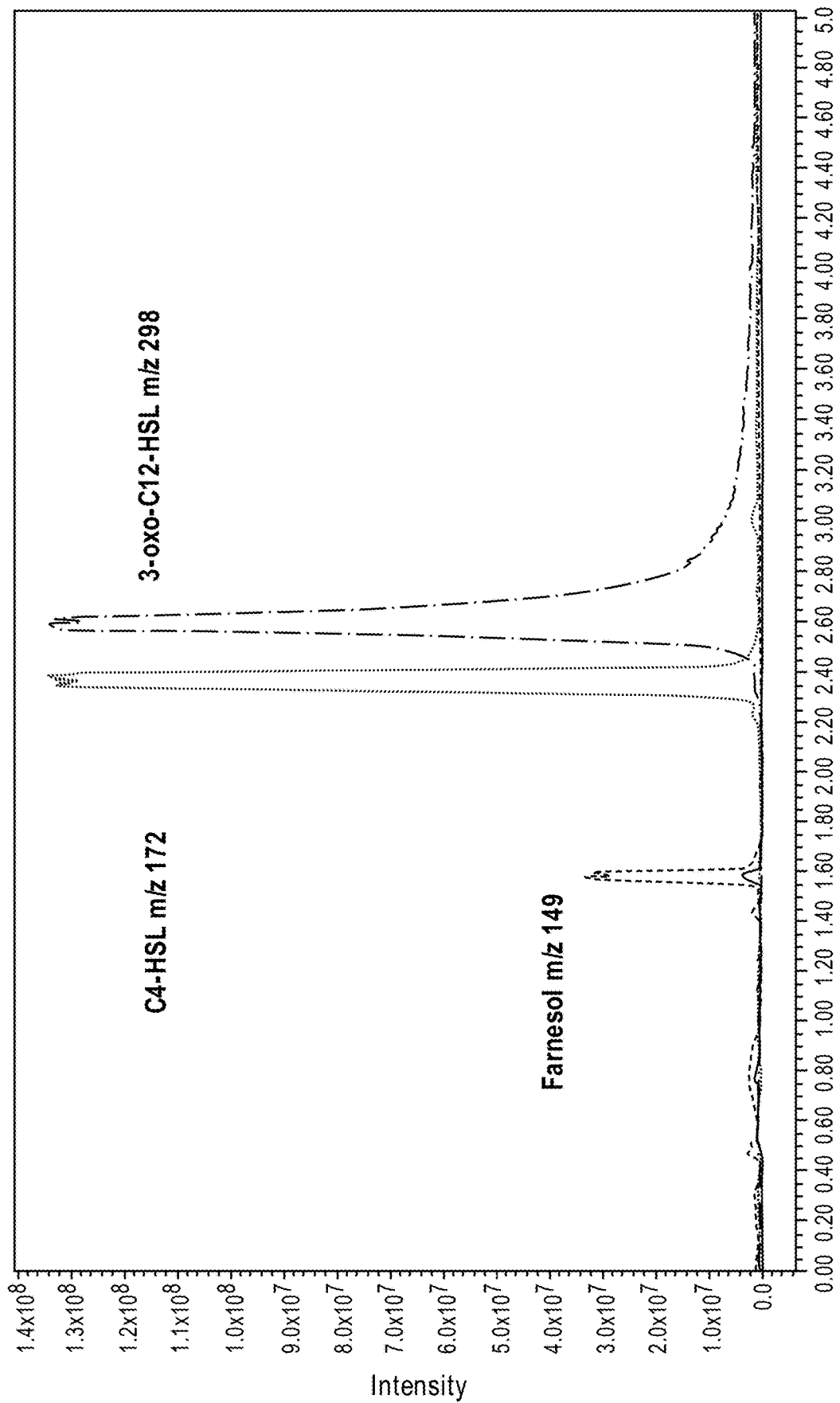
FIG. 4 is a chromatogram showing the peaks resulting from SFC/MS analysis of a sample containing three QSM standards: farnesol (peak 1), C4-HSL (peak 2), and C12-HSL (peak 3).

FIG. 1 is a three-dimensional chromatogram resulting from SFC/MS analysis of the QSM farnesol. FIG. 2 is a chromatograph resulting from SFC/MS analysis of the QSM N-Butyryl-DL-HSL (C4-HSL). FIG. 3 is a chromatograph resulting from SFC/MS analysis of the QSM 3-Oxo-C12-HSL (C12-HSL). FIG. 4 is a chromatogram showing the peaks resulting from SFC/MS analysis of a sample containing three QSM standards: farnesol (peak 1), C4-HSL (peak 2), and C12-HSL (peak 3).

For all experiments, the SFC parameters were as follows: System: ACQUITY UPC2 with PDA detector, Screening column: HSS C18, Mobile phase A: CO2, Modifier B: Methanol with 0.1% formic acid, Column temp.: 35° C. and ABPR: 2000 psi Flow rate: 2 mL/min, UV detection: 200-400 nm, Injection volume: 2 μL and the gradients are shown in Table 1.

TABLE 1

| Time (min) | Flow (ml/min) | % A(CO2) | % B | Curve |
|---|---|---|---|---|
| Initial | 2.000 | 100.0 | 0 | 6 |
| 1.70 | 2.000 | 95.0 | 5.0 | 8 |
| 4.90 | 2.000 | 80.0 | 20.0 | 8 |
| 5.00 | 2.000 | 100.0 | 0.0 | 8 |

The Mass spectrometer parameters were as follows: Capillary voltage: 4.6 kV, Cone voltage: 50 V, Extractor: 5 V, RF lens: 1.0 V, Source Temp.: 150° C., Desolvation temp.: 450° C., Cone gas: 120 L/h and Desolvation Gas Flow: 400 L/h.

In viewing FIG. 4, it can be seen that the three different QSMs were clearly separately detectable, even when contained in the sample, using the techniques, conditions, and parameters described above.

Figure 5:
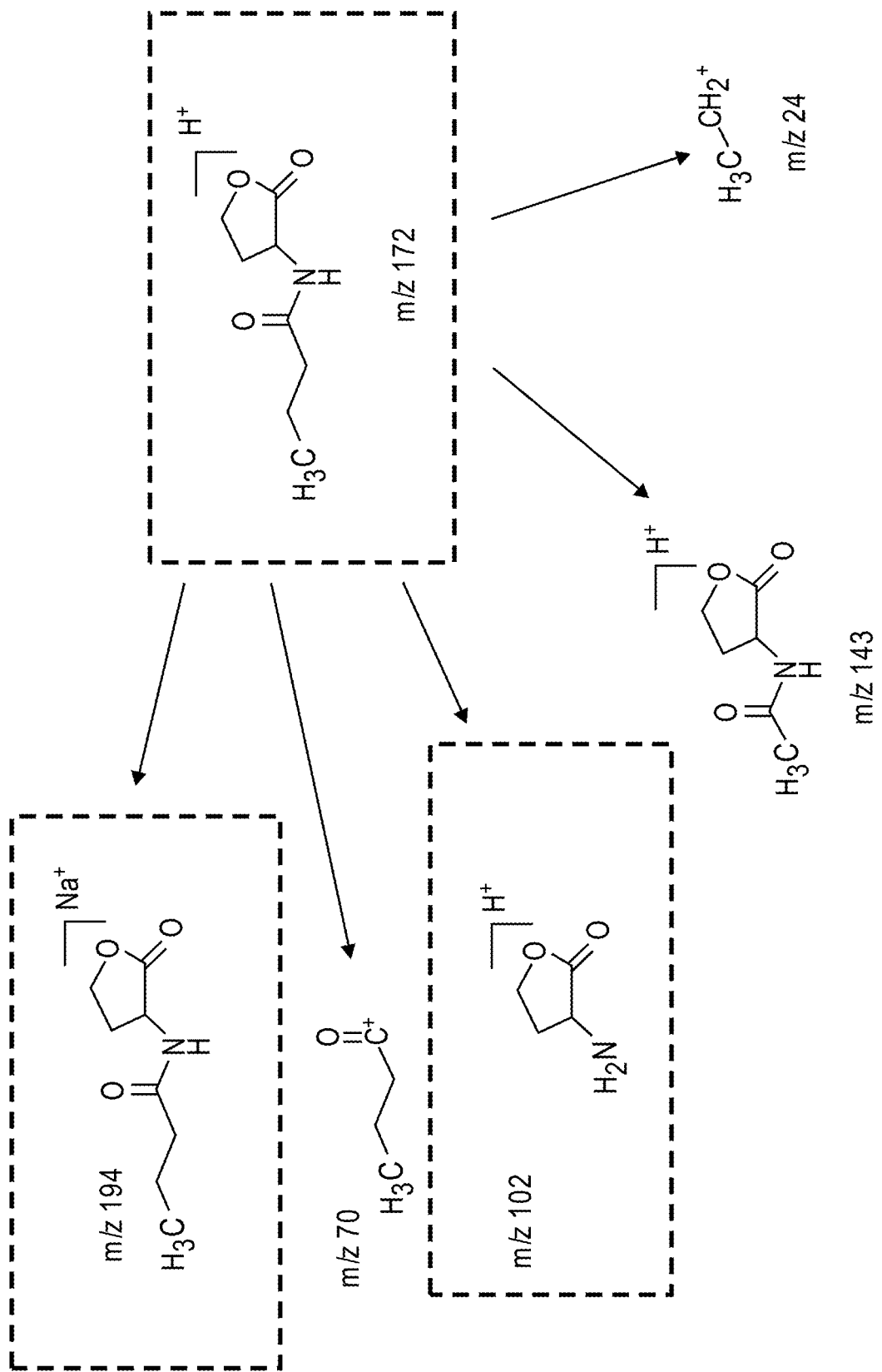
FIG. 5 shows the chemical structure and fragmentation ions for C4-HSL.
Figure 6:
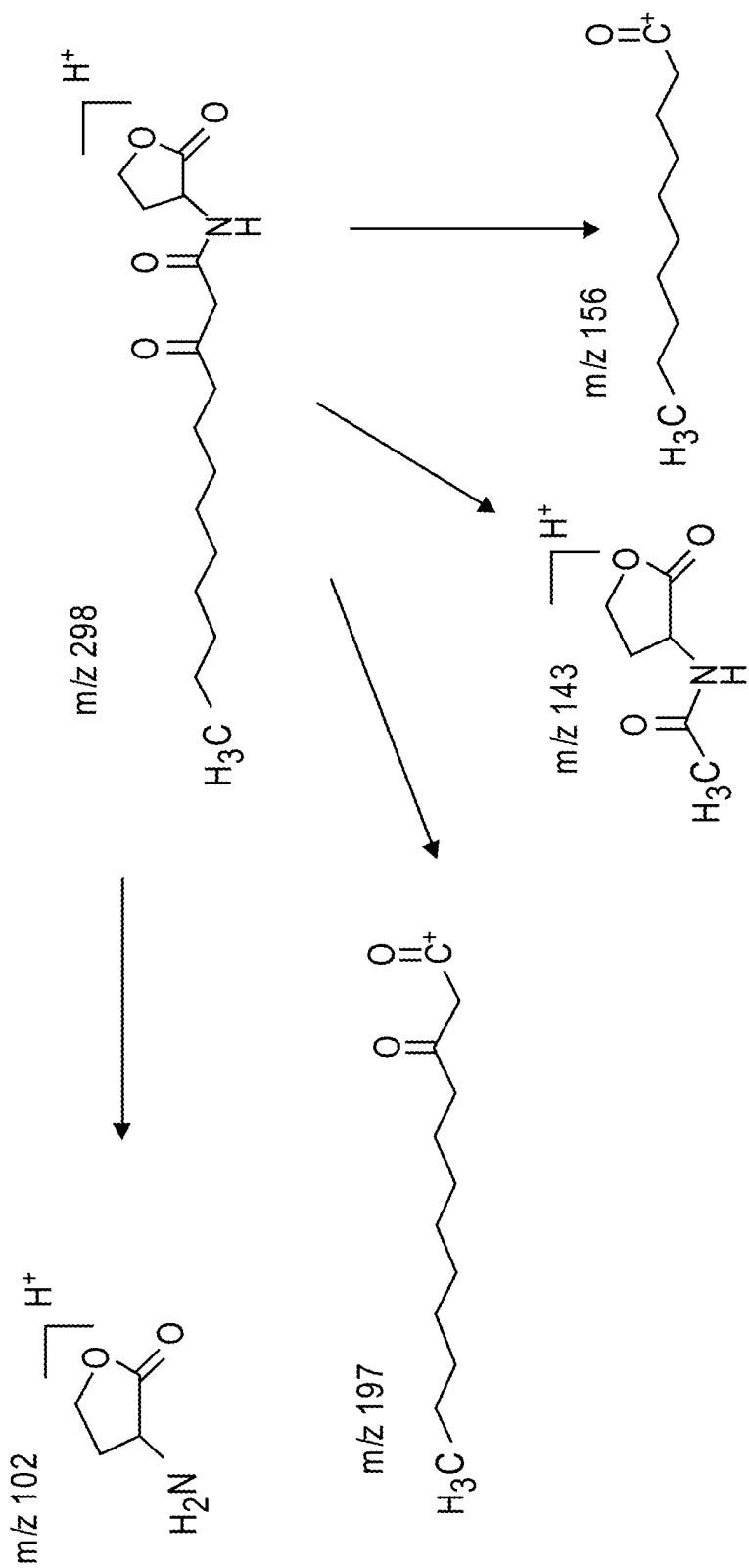
FIG. 6 shows the chemical structure and fragmentation ions for C12-HSL
Figure 7:
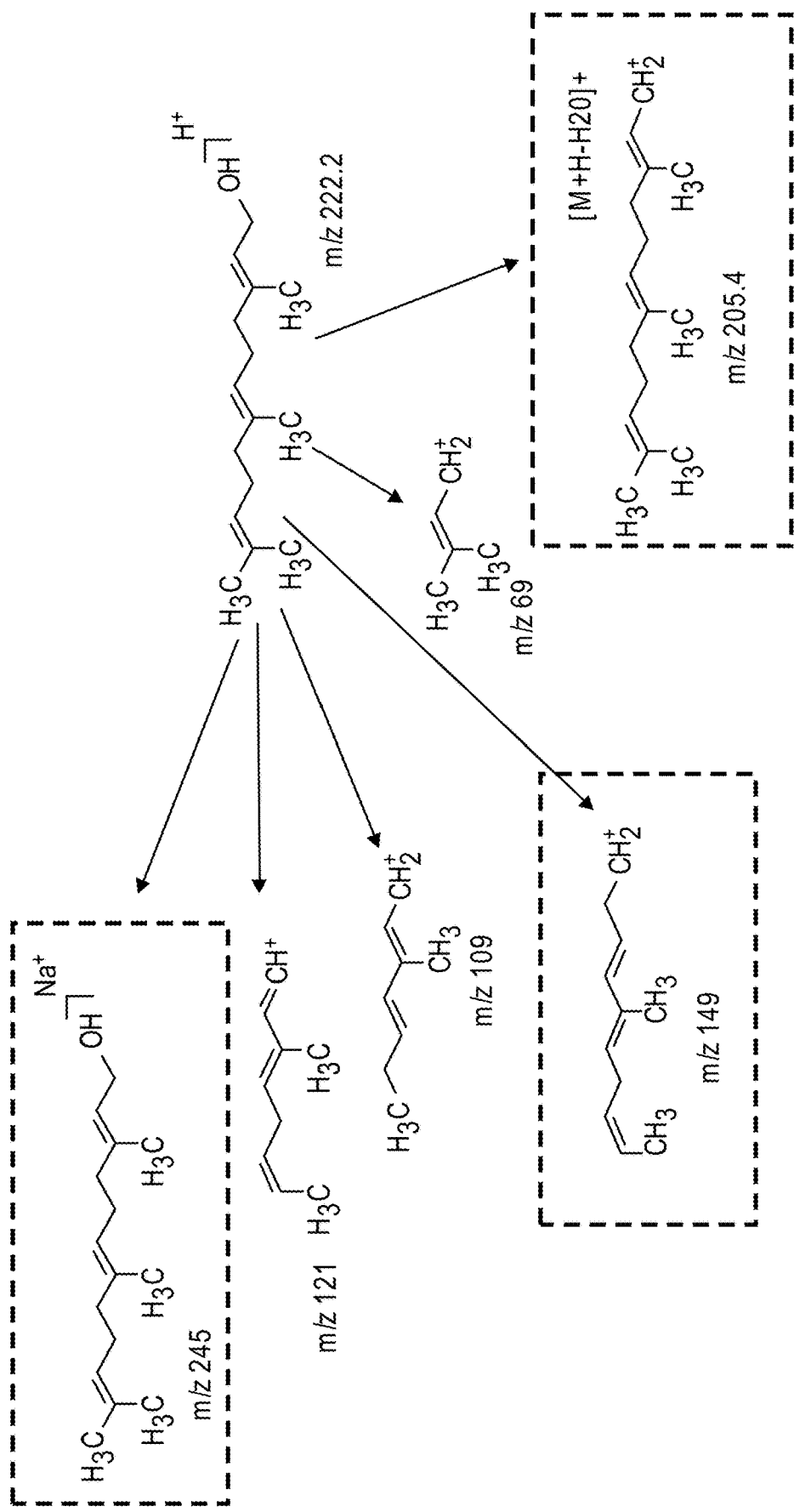
FIG. 7 shows the chemical structure and fragmentation ions for farnesol.
Figure 8:
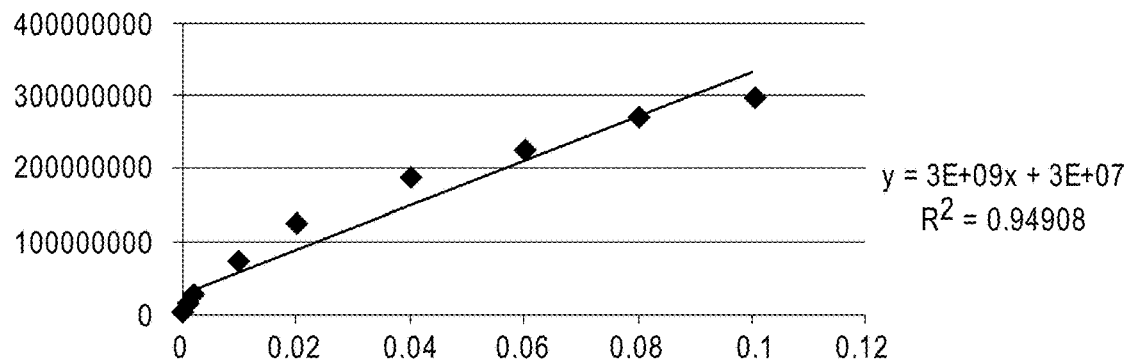
FIG. 8 is the standard curve for C4-HSL where m/z is 194.
Figure 9:
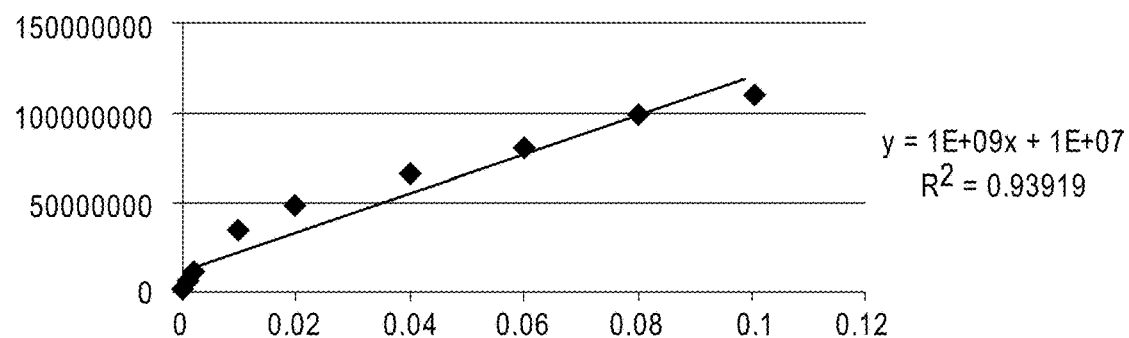
FIG. 9 is the standard curve for C4-HSL where m/z is 172.
Figure 10:
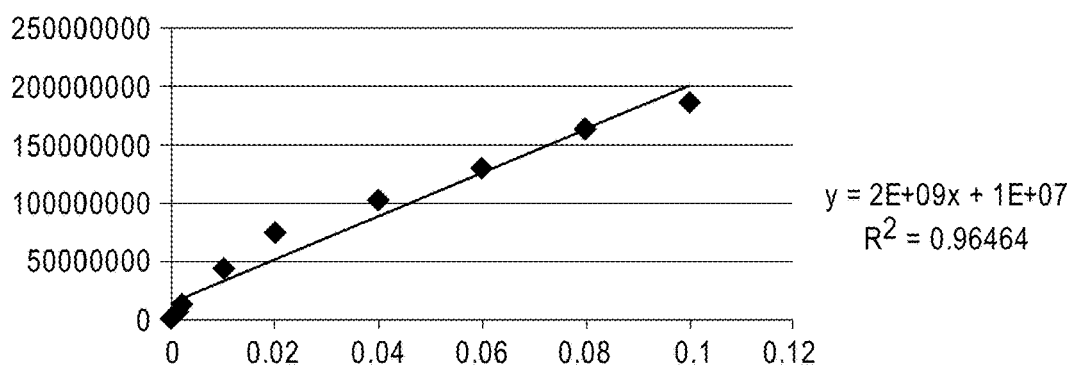
FIG. 10 is the standard curve for C4-HSL where m/z is 102
Figure 11:
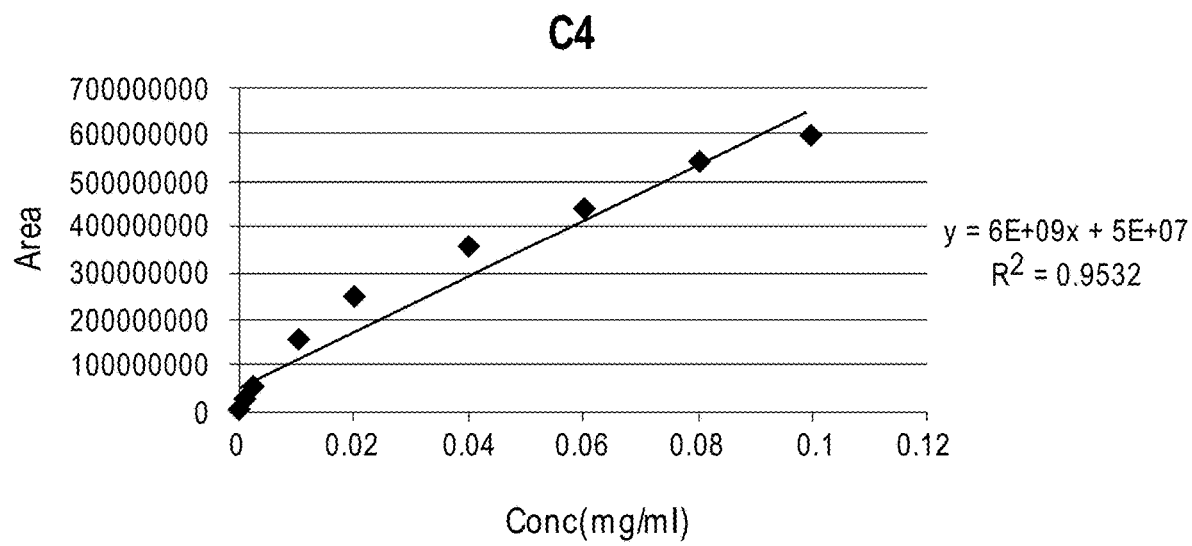
FIG. 11 is the standard curve for C4.
Figure 12:
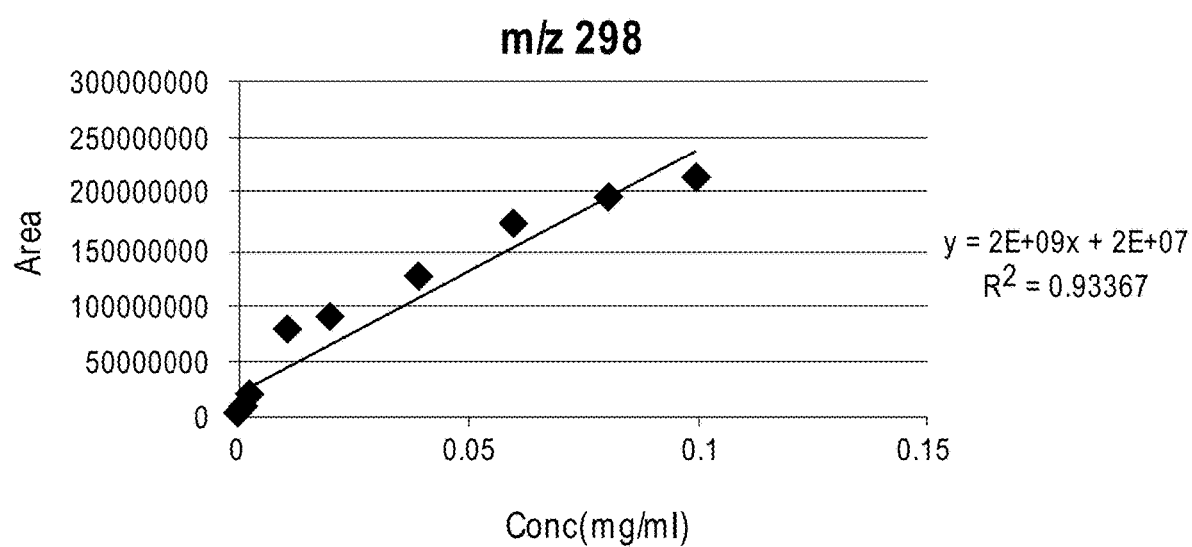
FIG. 12 is the standard curve for C12-HSL where m/z is 298.
Figure 13:
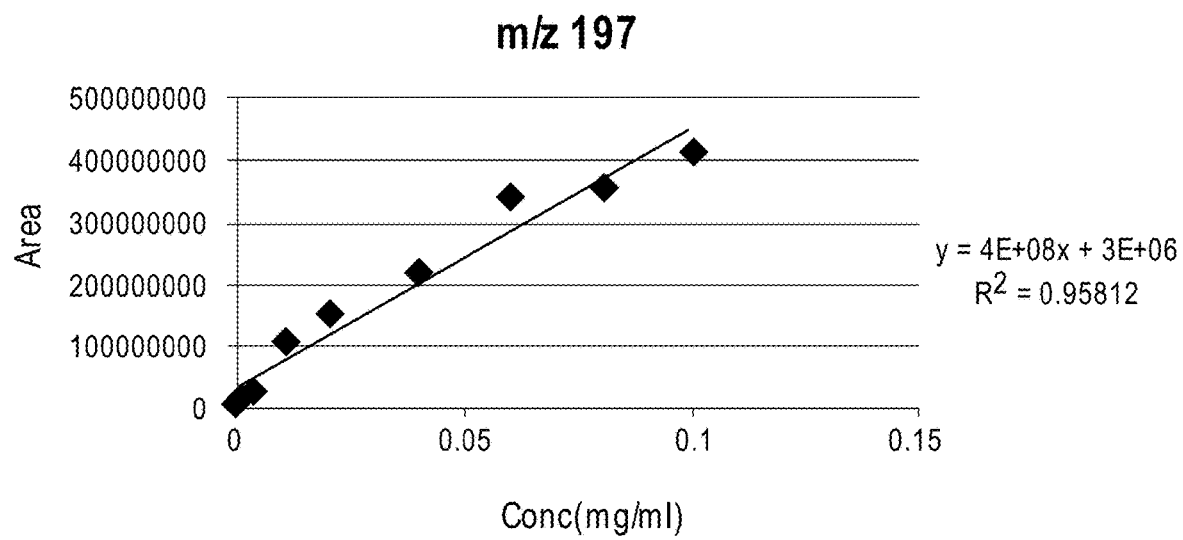
FIG. 13 is the standard curve for C12-HSL where m/z is 197.
Figure 14:
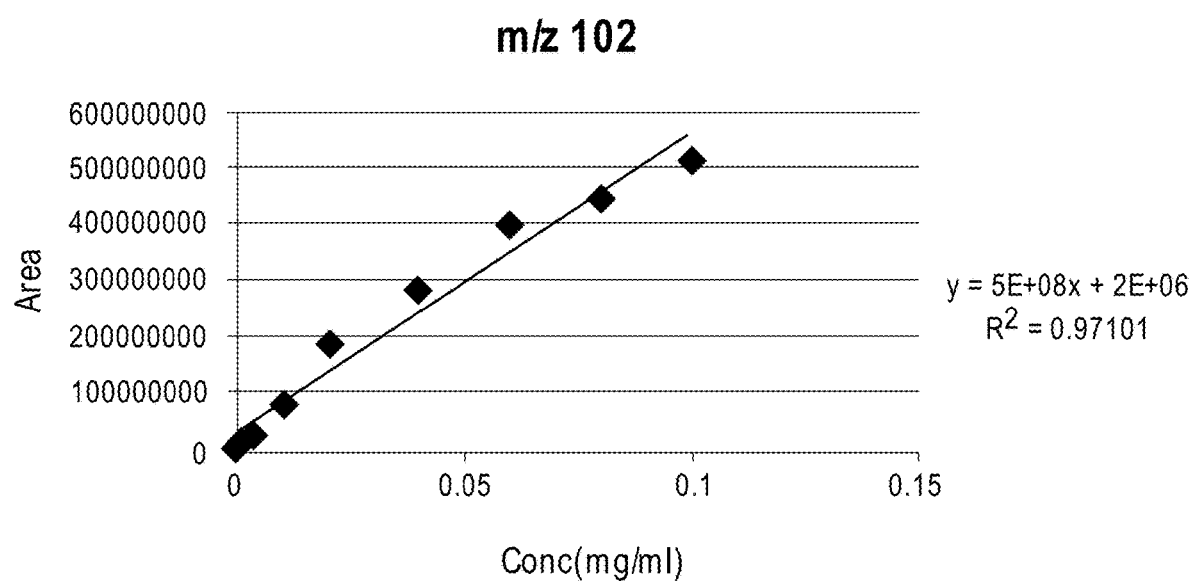
FIG. 14 is the standard curve for C12-HSL where m/z is 102.
Figure 15:
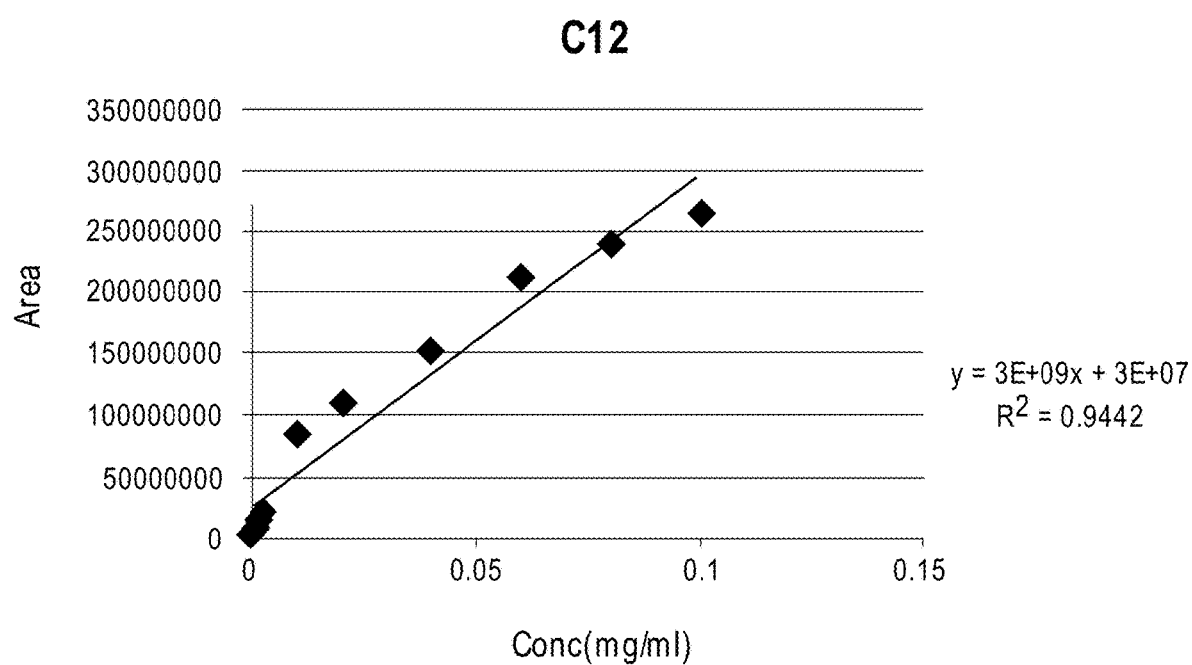
FIG. 15 is the standard curve for C12.
Figure 16:
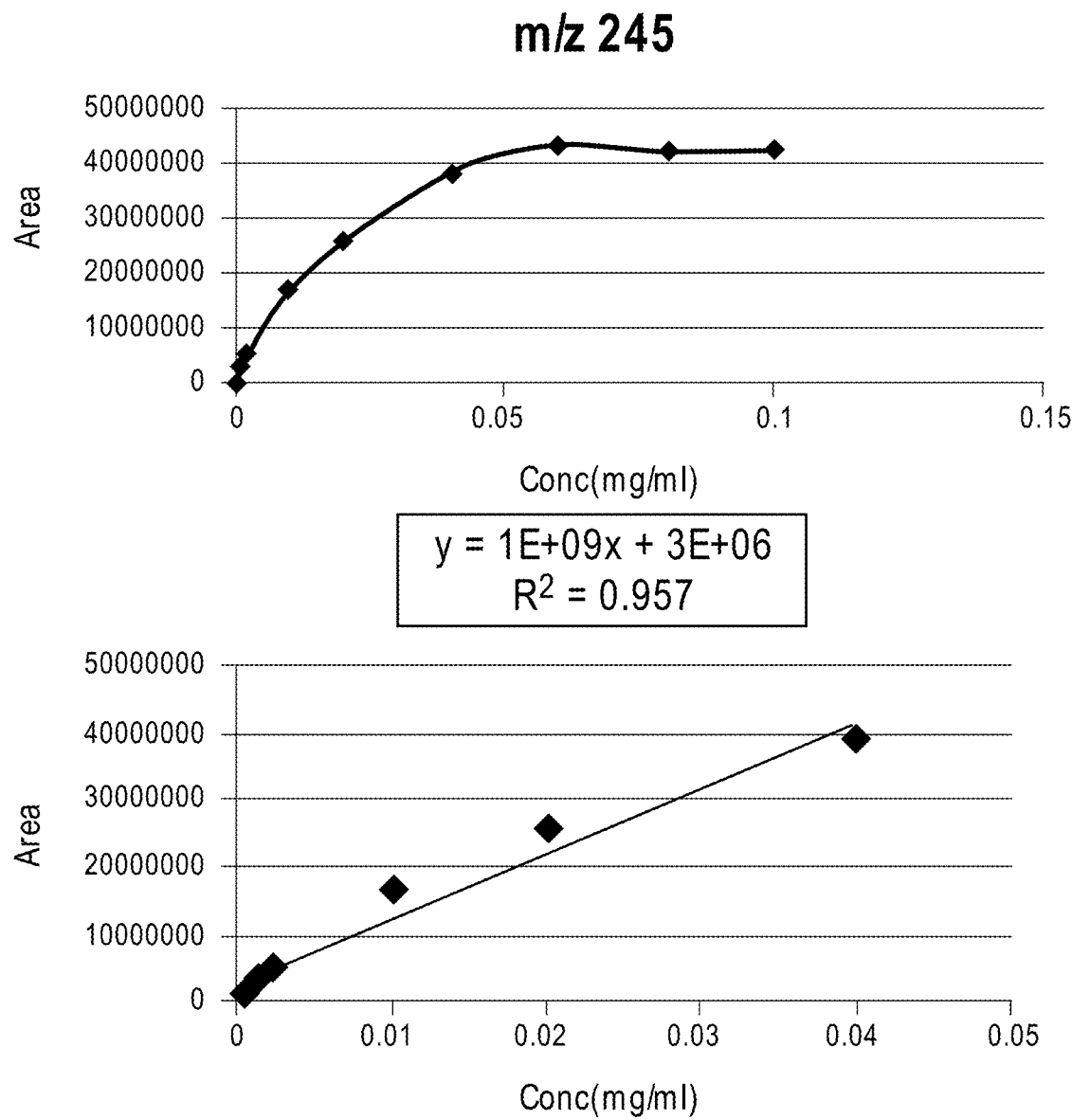
FIG. 16 is the standard curve for farnesol where m/z is 245.
Figure 17:
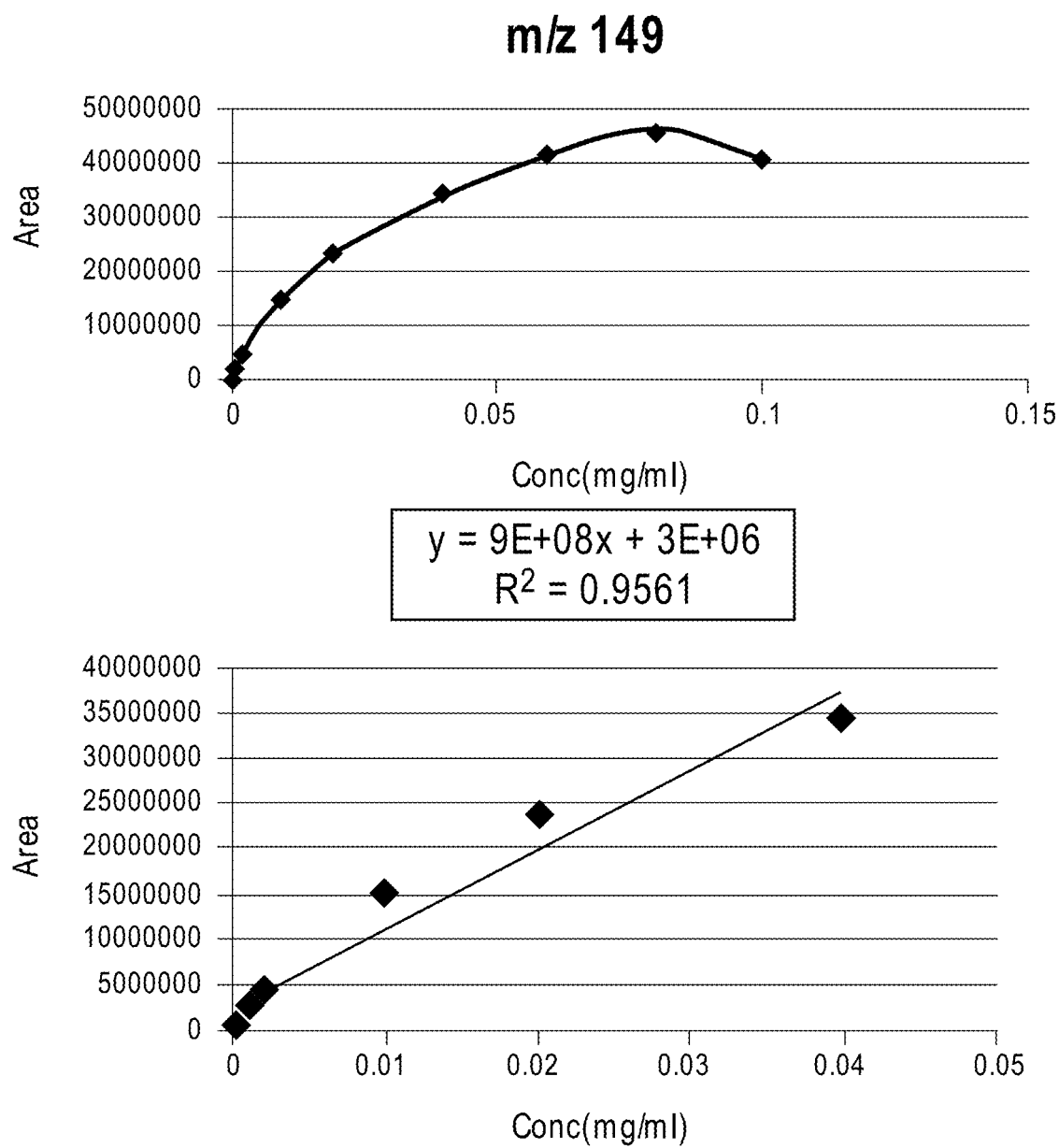
FIG. 17 is the standard curve for farnesol where m/z is 149.
Figure 18:
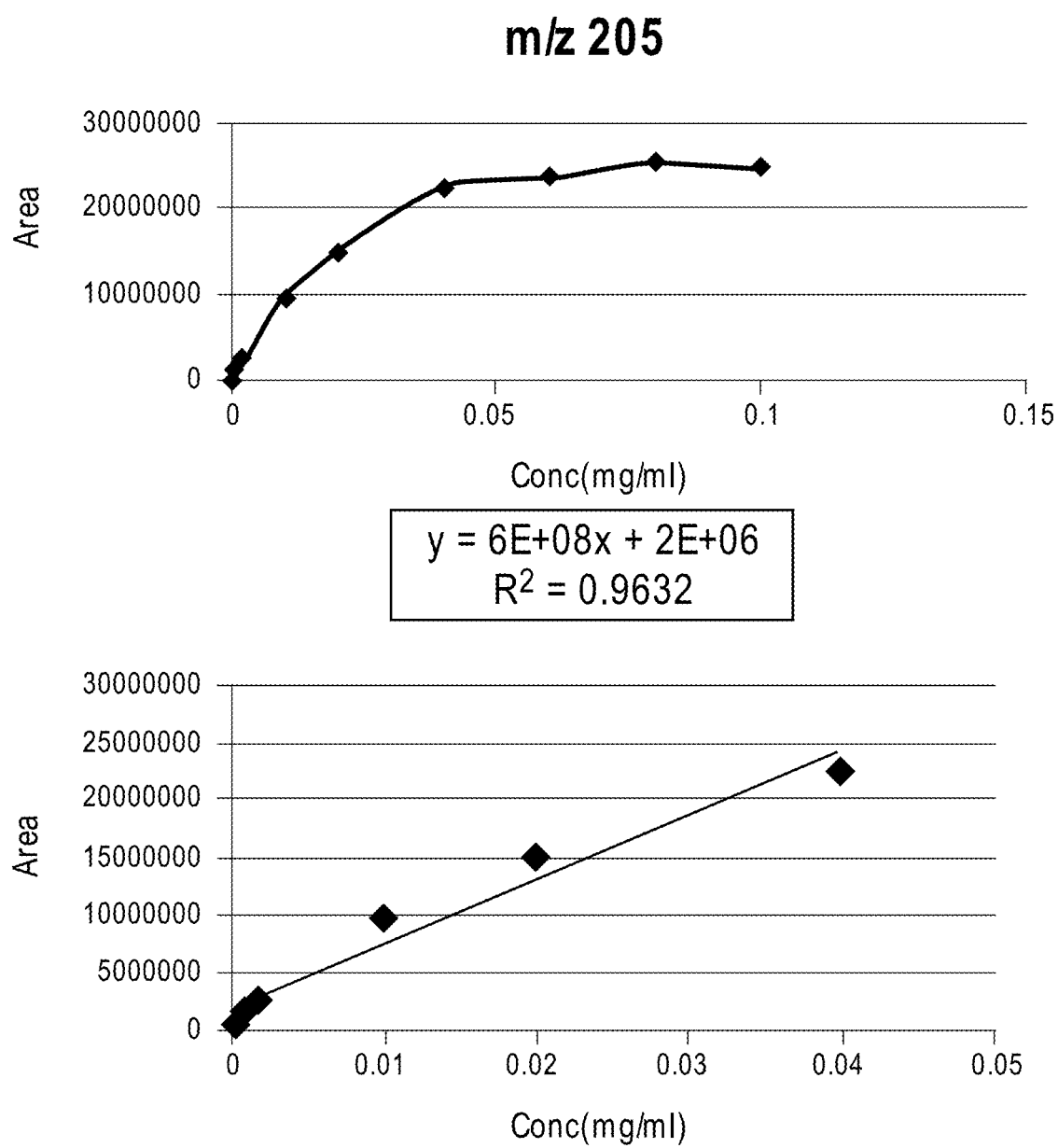
FIG. 18 is the standard curve for farnesol where m/z is 205.
Figure 19:
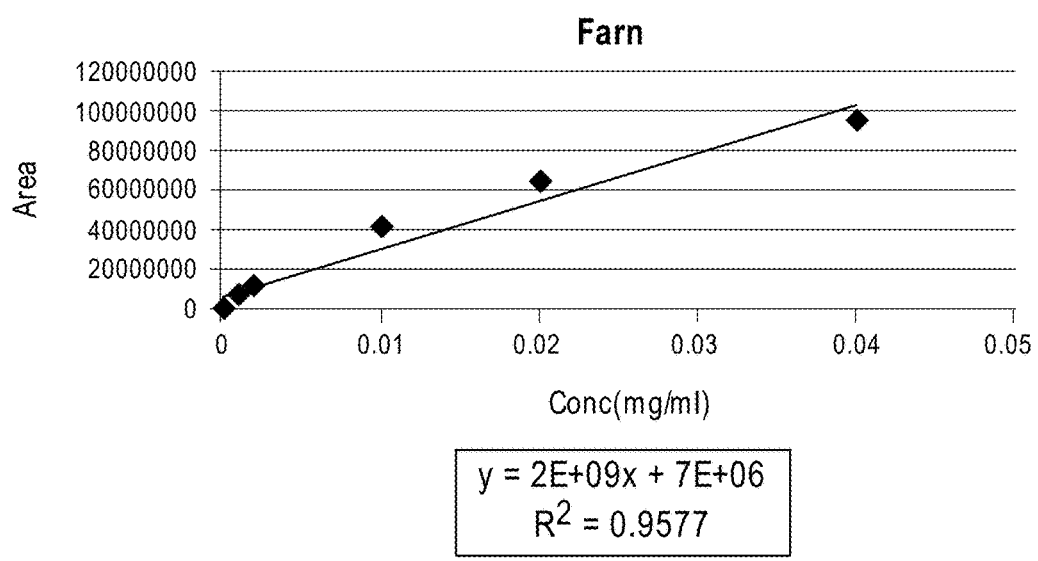
FIG. 19 is the standard curve for farnesol.

FIG. 5-7 show the original chemical structure for each QSM and exemplary fragmentation ions that were obtained using the parameters described above and which generated the peaks shown in FIGS. 1-4. FIG. 5 shows fragmentation ions for C4-HSL, FIG. 6 shows fragmentation ions for C12-HSL, and FIG. 7 shows fragmentation ions for farnesol. While these fragmentation ions were found to produce peaks that were separately distinguishable and suitable for identification, it will be understood that similarly suitable peaks could be obtained using different parameters and that such peaks and such parameters are considered to be within the scope of the present disclosure.

FIGS. 8-19 show standard curves for the QSMs studied above. FIGS. 8-11 are standard curves for C4-HSL, FIGS. 12-15 are standard curves for C12-HSL, and FIGS. 16-19 are standard curves for farnesol. This data demonstrates the linear response range and limits of detection and quantification and illustrates that the method described herein is suitable for quantifying QSMs and sufficiently sensitive to detect QSMs within anticipated ranges (i.e. those levels that one would expect to be able to find in contaminated samples after undergoing the procedures described above.)

It should be understood that other analytical methods in addition to SFC/MS can be used to detect QSMs for the purpose of diagnosing the presence of microbial organisms in clinical or other biological specimens. First, standard High-performance liquid chromatography (HPLC) or Ultra-high performance liquid chromatography coupled to appropriate detection technology, such as mass spectrometry, absorbance/fluorescence spectroscopy or spectrometry, or electrochemical detection, could be used to detect QSMs in specimens, similar to what is disclosed above. Second, after sample extraction and derivatization, if necessary, gas chromatography coupled with appropriate detection, such as flame ionization detection or mass spectrometry, could be used to detect QSMs in specimens, similar to what is disclosed above. Third, biochemical interaction assays wherein an affinity reagent (e.g., antibody) is bound to a surface (e.g., bead or well plate) and used to capture the analyte, followed by detection with a separate affinity reagent that is coupled to a moiety detectable by luminescent, fluorescent, colorimetric, enzymatic or spectroscopic/spectrometric methods could be used to detect QSMs in specimens, similar to what is disclosed above. Fourth, QSMs could be detected for the purposes elaborated herein using reagents that bind the QSM (e.g., a protein with a QSM binding domain), undergo a conformational change, and detect that conformational change by quantitative fluorescence spectroscopy methods, such as Forster Resonance Energy Transfer (FRET) between a donor and acceptor probe conjugated to the QSM binding reagent wherein the FRET signal is changed upon conformational change of the QSM binding reagent.

Accordingly, the methods described herein can be used to develop an information library comprising the chromatogram peaks that could be expected to be seen when a particular known microbial agent is present in a sample. Chromatograms from samples from patients, medical devices, etc. suspected of harboring such microbial agents could then be obtained and compared to the information library. The presence of a peak corresponding a known microbial agent would then be indicative of the presence of that microbial agent in the sample, while lack of a peak corresponding to a known microbial agent might be indicative of the non-presence of that particular microbial agent. This information could then be used, for example, to characterize any microbial agents present in the sample and/or diagnose or treat the patient from which the sample was obtained.

Detection of these compounds by this method provides a technique for rapid, culture free diagnosis of infection. QSMs associated with Gram-negative bacterial infections would indicate a Gram-negative bacterial infection and direct therapy to appropriate antibiotics. Likewise, QSMs associate with fungal pathogens like *C. albicans* would indicate Candidiasis and direct therapy to appropriate antimycotics. The presence of QSMs corresponding to multiple types of pathogens would alert medical personnel to the presence of a polymicrobial infection of the indicated pathogen types. Furthermore, the qualitative and quantitative pattern of QSMs detected may provide information about the stage of infectious disease and the involvement of microbial biofilms in the infectious pathogenesis.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a microbe" includes a plurality (for example, a culture or population) of such microbes, and so forth.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

All patents and publications referenced below and/or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

REFERENCES

1. Bertesteanu S, Triaridis S, Stankovic M, Lazar V, Chifiriuc M C, Vlad M, et al. Polymicrobial wound infections: pathophysiology and current therapeutic approaches. International journal of pharmaceutics. 2014; 463(2):119-26. Epub 2013/12/24. doi: 10.1016/j.ijpharm.2013.12.012. PubMed PMID: 24361265.
2. Jimenez P N, Koch G, Thompson J A, Xavier K B, Cool R H, Quax W J. The multiple signaling systems regulating virulence in *Pseudomonas aeruginosa*. Microbiol Mol Biol Rev. 2012; 76(1):46-65. Epub 2012/03/07. doi: 10.1128/MMBR.05007-11. PubMed PMID: 22390972; PubMed Central PMCID: PMC3294424.
3. Thoendel M, Kavanaugh J S, Flack C E, Horswill A R. Peptide signaling in the staphylococci. Chemical reviews. 2011; 111(1):117-51. Epub 2010/12/23. doi: 10.1021/cr100370n. PubMed PMID: 21174435; PubMed Central PMCID: PMC3086461.
4. Mallick E M, Bennett R J. Sensing of the microbial neighborhood by *Candida albicans*. PLoS Pathog. 2013; 9(10):e1003661. Epub 2013/11/10. doi: 10.1371/journal.ppat.1003661. PubMed PMID: 24204254; PubMed Central PMCID: PMC3814570.
5. Albuquerque P, Casadevall A. Quorum sensing in fungi—a review. Med Mycol. 2012; 50(4):337-45. Epub 2012/01/25. doi: 10.3109/13693786.2011.652201. PubMed PMID: 22268493.
6. Sully E K, Malachowa N, Elmore B O, Alexander S M, Femling J K, Gray B M, et al. Selective chemical inhibition of agr quorum sensing in *Staphylococcus aureus* promotes host defense with minimal impact on resistance. PLoS Pathog. 2014; 10(6):e1004174. Epub 2014/06/20. doi: 10.1371/journal.ppat.1004174. PubMed PMID: 24945495; PubMed Central PMCID: PMC4055767.
7. Piispanen A E, Grahl N, Hollomon J M, Hogan D A. Regulated proteolysis of *Candida albicans* Ras1 is involved in morphogenesis and quorum sensing regulation. Molecular microbiology. 2013; 89(1):166-78. Epub 2013/05/23. doi: 10.1111/mmi.12268. PubMed PMID: 23692372; PubMed Central PMCID: PMC3782256.
8. Lindsay A K, Deveau A, Piispanen A E, Hogan D A. Farnesol and cyclic AMP signaling effects on the hypha-to-yeast transition in *Candida albicans*. Eukaryot Cell.

2012; 11(10):1219-25. Epub 2012/08/14. doi: 10.1128/EC.00144-12. PubMed PMID: 22886999; PubMed Central PMCID: PMC3485915.
9. Tashiro M, Kimura S, Tateda K, Saga T, Ohno A, Ishii Y, et al. Pravastatin inhibits farnesol production in *Candida albicans* and improves survival in a mouse model of systemic candidiasis. Med Mycol. 2012; 50(4):353-60. Epub 2011/10/01. doi: 10.3109/13693786.2011.610037. PubMed PMID: 21954955.
10. Cheung G Y, Wang R, Khan B A, Sturdevant D E, Otto M. Role of the accessory gene regulator agr in community-associated methicillin-resistant *Staphylococcus aureus* pathogenesis. Infect Immun. 2011; 79(5):1927-35. Epub 2011/03/16. doi: 10.1128/IAI.00046-11. PubMed PMID: 21402769; PubMed Central PMCID: PMC3088142.
11. Imamura Y, Yanagihara K, Tomono K, Ohno H, Higashiyama Y, Miyazaki Y, et al. Role of *Pseudomonas aeruginosa* quorum-sensing systems in a mouse model of chronic respiratory infection. Journal of medical microbiology. 2005; 54(Pt 6):515-8. Epub 2005/05/13. doi: 10.1099/jmm.0.46004-0. PubMed PMID: 15888457.
12. Rocha C R, Schroppel K, Harcus D, Marcil A, Dignard D, Taylor B N, et al. Signaling through adenylyl cyclase is essential for hyphal growth and virulence in the pathogenic fungus *Candida albicans*. Mol Biol Cell. 2001; 12(11):3631-43. Epub 2001/11/06. PubMed PMID: 11694594; PubMed Central PMCID: PMC60281.
13. Painter K L, Krishna A, Wigneshweraraj S, Edwards A M. What role does the quorum-sensing accessory gene regulator system play during *Staphylococcus aureus* bacteremia? Trends Microbiol. 2014. Epub 2014/10/11. doi: 10.1016/j.tim.2014.09.002. PubMed PMID: 25300477.
14. Brown A J, Brown G D, Netea M G, Gow N A. Metabolism impacts upon Candida immunogenicity and pathogenicity at multiple levels. Trends Microbiol. 2014. Epub 2014/08/05. doi: 10.1016/j.tim.2014.07.001. PubMed PMID: 25088819; PubMed Central PMCID: PMC4222764.
15. DuMont A L, Yoong P, Surewaard B G, Benson M A, Nijland R, van Strijp J A, et al. *Staphylococcus aureus* elaborates leukocidin AB to mediate escape from within human neutrophils. Infect Immun. 2013; 81(5):1830-41. Epub 2013/03/20. doi: 10.1128/IAI.00095-13. PubMed PMID: 23509138; PubMed Central PMCID: PMC3648020.
16. Surewaard B G, de Haas C J, Vervoort F, Rigby K M, DeLeo F R, Otto M, et al. *Staphylococcal* alpha-phenol soluble modulins contribute to neutrophil lysis after phagocytosis. Cellular microbiology. 2013; 15(8):1427-37. Epub 2013/03/09. doi: 10.1111/cmi.12130. PubMed PMID: 23470014.
17. Geiger T, Francois P, Liebeke M, Fraunholz M, Goerke C, Krismer B, et al. The stringent response of *Staphylococcus aureus* and its impact on survival after phagocytosis through the induction of intracellular PSMs expression. PLoS Pathog. 2012; 8(11):e1003016. Epub 2012/12/05. doi: 10.1371/journal.ppat.1003016. PubMed PMID: 23209405; PubMed Central PMCID: PMC3510239.
18. Alonzo F, 3rd, Benson M A, Chen J, Novick R P, Shopsin B, Torres V J. *Staphylococcus aureus* leucocidin ED contributes to systemic infection by targeting neutrophils and promoting bacterial growth in vivo. Molecular microbiology. 2012; 83(2):423-35. Epub 2011/12/07. doi: 10.1111/j.1365-2958.2011.07942.x. PubMed PMID: 22142035; PubMed Central PMCID: PMC3258504.
19. Nair N, Biswas R, Gotz F, Biswas L. Impact of *Staphylococcus aureus* on pathogenesis in polymicrobial infections. Infect Immun. 2014; 82(6):2162-9. Epub 2014/03/20. doi: 10.1128/IAI.00059-14. PubMed PMID: 24643542; PubMed Central PMCID: PMC4019155.
20. Mear J B, Kipnis E, Faure E, Dessein R, Schurtz G, Faure K, et al. *Candida albicans* and *Pseudomonas aeruginosa* interactions: more than an opportunistic criminal association? Medecine et maladies infectieuses. 2013; 43(4):146-51. Epub 2013/04/30. doi: 10.1016/j.medmal.2013.02.005. PubMed PMID: 23622953.
21. De Sordi L, Muhlschlegel F A. Quorum sensing and fungal-bacterial interactions in *Candida albicans*: a communicative network regulating microbial coexistence and virulence. FEMS yeast research. 2009; 9(7):990-9. Epub 2009/10/22. PubMed PMID: 19845041.
22. Shirtliff M E, Peters B M, Jabra-Rizk M A. Cross-kingdom interactions: *Candida albicans* and bacteria. FEMS microbiology letters. 2009; 299(1):1-8. Epub 2009/06/26. doi: 10.1111/j.1574-6968.2009.01668.x. PubMed PMID: 19552706.
23. Morales D K, Grahl N, Okegbe C, Dietrich L E, Jacobs N J, Hogan D A. Control of *Candida albicans* metabolism and biofilm formation by *Pseudomonas aeruginosa* phenazines. mBio. 2013; 4(1):e00526-12. Epub 2013/01/31. doi: 10.1128/mBio.00526-12. PubMed PMID: 23362320; PubMed Central PMCID: PMC3560528.
24. Morales D K, Jacobs N J, Rajamani S, Krishnamurthy M, Cubillos-Ruiz J R, Hogan D A. Antifungal mechanisms by which a novel *Pseudomonas aeruginosa* phenazine toxin kills *Candida albicans* in biofilms. Molecular microbiology. 2010; 78(6):1379-92. Epub 2010/12/15. doi: 10.1111/j.1365-2958.2010.07414.x. PubMed PMID: 21143312; PubMed Central PMCID: PMC3828654.
25. Cugini C, Morales D K, Hogan D A. *Candida albicans*-produced farnesol stimulates *Pseudomonas* quinolone signal production in LasR-defective *Pseudomonas aeruginosa* strains. Microbiology. 2010; 156(Pt 10):3096-107. Epub 2010/07/27. doi: 10.1099/mic.0.037911-0. PubMed PMID: 20656785; PubMed Central PMCID: PMC3068698.
26. Cugini C, Calfee M W, Farrow J M, 3rd, Morales D K, Pesci E C, Hogan D A. Farnesol, a common sesquiterpene, inhibits PQS production in *Pseudomonas aeruginosa*. Molecular microbiology. 2007; 65(4):896-906. Epub 2007/07/21. doi: 10.1111/j.1365-2958.2007.05840.x. PubMed PMID: 17640272.
27. Azoulay E, Timsit J F, Tafflet M, de Lassence A, Darmon M, Zahar J R, et al. Candida colonization of the respiratory tract and subsequent pseudomonas ventilator associated pneumonia. Chest. 2006; 129(1):110-7. Epub 2006/01/21. doi: 10.1378/chest.129.1.110. PubMed PMID: 16424420.
28. Hogan D A, Kolter R. *Pseudomonas-Candida* interactions: an ecological role for virulence factors. Science. 2002; 296(5576):2229-32. Epub 2002/06/22. doi: 10.1126/science.1070784. PubMed PMID: 12077418.
29. McKenzie H, Hayes L, White K, Cox K, Fethney J, Boughton M, et al. Chemotherapy outpatients' unplanned presentations to hospital: a retrospective study. Supportive care in cancer: official journal of the Multinational Association of Supportive Care in Cancer. 2011; 19(7): 963-9. Epub 2010/05/26. doi: 10.1007/s00520-010-0913-y. PubMed PMID: 20499108.
30. Rosa R G, Goldani L Z. Cohort study of the impact of time to antibiotic administration on mortality in patients with febrile neutropenia. Antimicrobial agents and chemotherapy. 2014; 58(7):3799-803. Epub 2014/04/23. doi: 10.1128/AAC.02561-14. PubMed PMID: 24752269; PubMed Central PMCID: PMC4068526.
31. Freifeld A G, Bow E J, Sepkowitz K A, Boeckh M J, Ito J I, Mullen C A, et al. Clinical practice guideline for the use of antimicrobial agents in neutropenic patients with cancer: 2010 update by the infectious diseases society of america. Clin Infect Dis. 2011; 52(4):e56-93. Epub 2011/01/25. doi: 10.1093/cid/cir073. PubMed PMID: 21258094.
32. Ortori C A, Halliday N, Camara M, Williams P, Barrett D A. LC-MS/MS quantitative analysis of quorum sensing signal molecules. Methods Mol Biol. 2014; 1149:255-70. Epub 2014/05/14. doi: 10.1007/978-1-4939-0473-0_21. PubMed PMID: 24818911.
33. Junio H A, Todd D A, Ettefagh K A, Ehrmann B M, Kavanaugh J S, Horswill A R, et al. Quantitative analysis of autoinducing peptide I (AIP-I) from *Staphylococcus aureus* cultures using ultrahigh performance liquid chromatography-high resolving power mass spectrometry. Journal of chromatography B, Analytical technologies in the biomedical and life sciences. 2013; 930:7-12. Epub 2013/05/25. doi: 10.1016/j.jchromb.2013.04.019. PubMed PMID: 23703543; PubMed Central PMCID: PMC3717363.
34. Struss A K, Nunes A, Waalen J, Lowery C A, Pullanikat P, Denery J R, et al. Toward implementation of quorum sensing autoinducers as biomarkers for infectious disease states. Analytical chemistry. 2013; 85(6):3355-62. Epub 2013/02/09. doi: 10.1021/ac400032a. PubMed PMID: 23391272; PubMed Central PMCID: PMC3604138.
35. Gregus P, Vlckova H, Buchta V, Kestranek J, Krivcikova L, Novakova L. Ultra high performance liquid chromatography tandem mass spectrometry analysis of quorum-sensing molecules of *Candida albicans*. Journal of pharmaceutical and biomedical analysis. 2010; 53(3):674-81. Epub 2010/06/29. doi: 10.1016/j.jpba.2010.05.029. PubMed PMID: 20580513.
36. Hornby J M, Jensen E C, Lisec A D, Tasto J J, Jahnke B, Shoemaker R, et al. Quorum sensing in the dimorphic fungus *Candida albicans* is mediated by farnesol. Applied and environmental microbiology. 2001; 67(7):2982-92. Epub 2001/06/27. doi: 10.1128/AEM.67.7.2982-2992.2001. PubMed PMID: 11425711; PubMed Central PMCID: PMC92970.
37. Chotirmall S H, Greene C M, McElvaney N G. *Candida* species in cystic fibrosis: A road less travelled. Med Mycol. 2010; 48 Suppl 1:S114-24. Epub 2010/11/12. doi: 10.3109/13693786.2010.503320. PubMed PMID: 21067323.
38. Sagel S D, Gibson R L, Emerson J, McNamara S, Burns J L, Wagener J S, et al. Impact of *Pseudomonas* and *Staphylococcus* infection on inflammation and clinical status in young children with cystic fibrosis. J Pediatr. 2009; 154(2):183-8. Epub 2008/09/30. doi: 10.1016/j.jpeds.2008.08.001. PubMed PMID: 18822427; PubMed Central PMCID: PMC2654617.
39. Emerson J, Rosenfeld M, McNamara S, Ramsey B, Gibson R L. *Pseudomonas aeruginosa* and other predictors of mortality and morbidity in young children with cystic fibrosis. Pediatric pulmonology. 2002; 34(2):91-100. Epub 2002/07/12. doi: 10.1002/ppul.10127. PubMed PMID: 12112774.
40. Sievert D M, Ricks P, Edwards J R, Schneider A, Patel J, Srinivasan A, et al. Antimicrobial-resistant pathogens associated with healthcare-associated infections: summary of data reported to the National Healthcare Safety Network at the Centers for Disease Control and Prevention, 2009-2010. Infection control and hospital epidemiology: the official journal of the Society of Hospital Epidemiologists of America. 2013; 34(1):1-14. Epub 2012/12/12. doi: 10.1086/668770. PubMed PMID: 23221186.
41. Ozer E A, Pezzulo A, Shih D M, Chun C, Furlong C, Lusis A J, et al. Human and murine paraoxonase 1 are host modulators of *Pseudomonas aeruginosa* quorumsensing. FEMS microbiology letters. 2005; 253(1):29-37. Epub 2005/11/02. doi: 10.1016/j.femsle.2005.09.023. PubMed PMID: 16260097.
42. Yang F, Wang L H, Wang J, Dong Y H, Hu J Y, Zhang L H. Quorum quenching enzyme activity is widely conserved in the sera of mammalian species. FEBS Lett. 2005; 579(17):3713-7. Epub 2005/06/21. doi: 10.1016/j.febslet.2005.05.060. PubMed PMID: 15963993.
43. Dong Y H, Wang L H, Xu J L, Zhang H B, Zhang X F, Zhang L H. Quenching quorum-sensing-dependent bacterial infection by an N-acyl homoserine lactonase. Nature. 2001; 411(6839):813-7. Epub 2001/07/19. doi: 10.1038/35081101. PubMed PMID: 11459062.
44. Kumar R, Chhibber S, Gupta V, Harjai K. Screening & profiling of quorum sensing signal molecules in *Pseudomonas aeruginosa* isolates from catheterized urinary tract infection patients. The Indian journal of medical research. 2011; 134:208-13. Epub 2011/09/14. PubMed PMID: 21911974; PubMed Central PMCID: PMC3181022.
45. Massai F, Imperi F, Quattrucci S, Zennaro E, Visca P, Leoni L. A multitask biosensor for micro-volumetric detection of N-3-oxo-dodecanoyl-homoserine lactone quorum sensing signal. Biosensors & bioelectronics. 2011; 26(8):3444-9. Epub 2011/02/18. doi: 10.1016/j.bios.2011.01.022. PubMed PMID: 21324665.
46. Baldrich E, Munoz F X, Garcia-Aljaro C. Electrochemical detection of quorum sensing signaling molecules by dual signal confirmation at microelectrode arrays. Analytical chemistry. 2011; 83(6):2097-103. Epub 2011/02/18. doi: 10.1021/ac1028243. PubMed PMID: 21323339.
47. Nakagami G, Sanada H, Sugama J, Morohoshi T, Ikeda T, Ohta Y. Detection of *Pseudomonas aeruginosa* quorum sensing signals in an infected ischemic wound: an experimental study in rats. Wound repair and regeneration: official publication of the Wound Healing Society [and] the European Tissue Repair Society. 2008; 16(1):30-6. Epub 2008/01/24. doi: 10.1111/j.1524-475X.2007.00329.x. PubMed PMID: 18211577.

What is claimed is:

1. A method for characterizing QSMs associated with microbial infections, the method comprising:
  obtaining a sample comprising a first QSM associated with a bacterium and a second QSM associated with a fungus;
  extracting the first and second QSMs if the sample comprises contaminants;
  subjecting the first and second QSMs to supercritical fluid chromatography and mass spectrometry (SFC/MS) to obtain a chromatogram of the first and second QSMs and associating the peaks in the chromatogram with the first and second QSMs; and
  wherein the conditions under which the QSMs are extracted and the SFC/MS are performed is optimized to produce a single chromatogram displaying multiple separately distinguishable chromatogram peaks for the first and second QSMs.

2. The method of claim 1 wherein the peaks enable the identification of and distinction between QSMs produced by gram positive bacteria, gram negative bacteria and fungus.

3. The method of claim 1 wherein the extracted QSMs are selected from the group consisting of farnesol, C4-HSL and 3-oxo-C12-HSL.

4. The method of claim 1 wherein the extracted QSMs are reconstituted or dissolved in a solvent comprising methanol and formic acid.

5. The method of claim 1 further comprising repeating the method to obtain a plurality of chromatograms, thus producing a library of QSM chromatograms, wherein the chromatograms associate various QSM chromatogram peaks with one or more microbes.

6. The method of claim 5 wherein the library includes QSM chromatograms that distinguish between QSMs associated with gram positive bacteria and gram negative bacteria.

7. The method of claim 5 wherein the library includes QSM chromatograms that distinguish between QSMs associated with bacteria and fungi.

8. The method of claim 5 wherein the library includes QSM chromatograms that distinguish between QSMs associated with *C. albicans* and *P. aeruginosa*.

\* \* \* \* \*